United States Patent
Taylor et al.

(10) Patent No.: US 11,197,749 B2
(45) Date of Patent: Dec. 14, 2021

(54) TIME DEPENDENT PHYSIOLOGIC TISSUE SCAFFOLD

(71) Applicant: POLY-MED, INC., Anderson, SC (US)

(72) Inventors: Michael Scott Taylor, Anderson, SC (US); Seth Dylan McCullen, Greenville, SC (US); Kenneth W. Clinkscales, Easley, SC (US); Georgios T. Hilas, Bloomington, IN (US)

(73) Assignee: POLY-MED, INC., Anderson, SC (US)

( * ) Notice: Subject to any disclaimer, the term of this patent is extended or adjusted under 35 U.S.C. 154(b) by 0 days.

(21) Appl. No.: 15/768,463

(22) PCT Filed: Nov. 4, 2016

(86) PCT No.: PCT/US2016/060682
§ 371 (c)(1),
(2) Date: Apr. 13, 2018

(87) PCT Pub. No.: WO2017/079659
PCT Pub. Date: May 11, 2017

(65) Prior Publication Data
US 2018/0303592 A1    Oct. 25, 2018

Related U.S. Application Data

(60) Provisional application No. 62/250,568, filed on Nov. 4, 2015.

(51) Int. Cl.
*A61F 2/00* (2006.01)
*D04B 21/12* (2006.01)

(52) U.S. Cl.
CPC ............ *A61F 2/0063* (2013.01); *D04B 21/12* (2013.01); *A61F 2002/0068* (2013.01);
(Continued)

(58) Field of Classification Search
CPC .................. A61F 2/0063–2002/0068; A61F 2250/003–0031; D04B 21/12; D10B 2509/08
See application file for complete search history.

(56) References Cited

U.S. PATENT DOCUMENTS 3,272,204 A    9/1966  Artandi et al.
6,162,962 A *  12/2000  Hinsch .................. A61L 31/148
                                         623/11.11
(Continued)

FOREIGN PATENT DOCUMENTS

CN    202010683628.1    11/2016
CN    201680063840.X    8/2020
(Continued)

OTHER PUBLICATIONS

International Search Report and Written Opinion dated Jan. 24, 2017, for International Application No. PCT/US2016/060682.
Singapore Written Opinion, dated Jul. 10, 2019, in Singapore Patent Appplication No. 11201803220U, which is a national phase application of PCT/US2016/060682, as is U.S. Appl. No. 15/768,463.
English translation of Japanese Patent Office Action, dated Dec. 18, 2020, 4 p.
(Continued)

*Primary Examiner* — Shaun L David
*Assistant Examiner* — Brigid K Byrd

(57) ABSTRACT

A fabric or mesh construct, and process for making same, which allows for early wound stability and then transitions to a more compliant state exhibiting a substantially constant macro-porous pore structure through the life of the implant to promote good tissue incorporation without bridging.

13 Claims, 4 Drawing Sheets

(52) U.S. Cl.
CPC . *A61F 2240/001* (2013.01); *A61F 2250/0031* (2013.01); *A61F 2250/0067* (2013.01); *D10B 2401/12* (2013.01); *D10B 2509/08* (2013.01)

(56) References Cited

U.S. PATENT DOCUMENTS

| | | | |
|---|---|---|---|
| 6,966,918 B1* | 11/2005 | Schuldt-Hempe | A61F 2/0063 606/151 |
| 2004/0029478 A1 | 2/2004 | Planck | |
| 2005/0070930 A1 | 3/2005 | Kammerer | |
| 2005/0288797 A1 | 12/2005 | Howland | |
| 2007/0282160 A1* | 12/2007 | Sheu | A61F 2/0045 600/30 |
| 2008/0119848 A1 | 5/2008 | Shalaby et al. | |
| 2009/0171377 A1 | 7/2009 | Intoccia et al. | |
| 2011/0166494 A1* | 7/2011 | Calvez | A61F 2/0063 604/8 |
| 2011/0301717 A1* | 12/2011 | Becker | A61L 31/148 623/23.72 |
| 2012/0330093 A1 | 12/2012 | Odermatt et al. | |
| 2013/0012768 A1* | 1/2013 | Koullick | A61L 31/148 600/37 |
| 2013/0103060 A1 | 4/2013 | Stopek et al. | |
| 2013/0172994 A1 | 7/2013 | Hilton | |
| 2013/0184722 A1* | 7/2013 | Stopek | A61F 2/0063 606/151 |
| 2013/0267137 A1* | 10/2013 | Peniston | A61F 2/0063 442/50 |
| 2013/0317623 A1 | 11/2013 | Trabucco | |
| 2016/0058533 A1* | 3/2016 | Schuldt-Hempe | A61F 2/0063 606/151 |

FOREIGN PATENT DOCUMENTS

| | | |
|---|---|---|
| EP | 07109992.3 | 12/2008 |
| EP | 3370640 | 6/2020 |
| IN | 370674 | 6/2021 |
| JP | 2018-543066 | 11/2016 |
| SG | 11201803220 U | 11/2016 |
| WO | WO 2011/103141 | 8/2011 |

OTHER PUBLICATIONS

English translation of Patent Certificate, issued 202-08-11, in Chinese Patent Application No. 201680063840.X, national phase of PCT/US2016/060682, filed Nov. 4, 2016, 2 p.
Notice to Grant, dated Apr. 30, 2020, in Chinese Patent Application No. 201680063840.X, national phase of PCT/US2016/060682, filed Nov. 4, 2016, 4 p.
Rejection Decision, dated Oct. 11, 2019, in Chinese Patent Application No. 201680063840.X, national phase of PCT/US2016/060682, filed Nov. 4, 2016, 8 p.
First Office Action, dated Apr. 4, 2019, in Chinese Patent Application No. 201680063840.X, national phase of PCT/US2016/060682, filed Nov. 4, 2016, 7 p.
Decision to Grant, dated May 28, 2020, in EPO Patent Application No. 16863104.2, national phase of PCT/US2016/060682, filed Nov. 4, 2016, 2 p.
Extended EPO Search Report, dated Jun. 27, 2019, national phase of PCT/US2016/060682, filed Nov. 4, 2016, 7 p.
Intimation of Grant, dated Jun. 30, 2021, in Indian Patent Application No. 201817019733, national phase of PCT/US2016/060682, filed Nov. 4, 2016, 1 p.
Hearing Notice, issued Jun. 4, 2021, in Indian Patent Application No. 201817019733, national phase of PCT/US2016/060682, filed Nov. 4, 2016, 2 p.
First Office Action, dated Aug. 16, 2020, in Indian Patent Application No. 201817019733, national phase of PCT/US2016/060682, filed Nov. 4, 2016, 5 p.
Decision to Grant, dated Jul. 19, 2021, in Japanese Patent Application No. 2018-543066, national phase of PCT/US2016/060682, filed Nov. 4, 2016, 2 p.
Office Action, dated Dec. 3, 2020, in Japanese Patent Application No. 2018-543066, national phase of PCT/US2016/060682, filed Nov. 4, 2016, 5 p.
2nd Written Opinion, dated Nov. 12, 2020, in Singaporean Patent Application No. 11201803220U, national phase of PCT/US2016/060682, filed Apr. 4, 2016, 5 p.
1st Written Opinion, dated Jul. 10, 2019, in Singaporean Patent Application No. 11201803220U, national phase of PCT/US2016/060682, filed Nov. 4, 2016, 6 p.

* cited by examiner

TIME DEPENDENT PHYSIOLOGIC TISSUE SCAFFOLD

CROSS-REFERENCE TO RELATED APPLICATION

This application is a national phase application under 35 U.S.C. § 371 of International Application No. PCT/US2016/060682, filed Nov. 4, 2016, claims the benefit under 35 U.S.C. § 119(e) of U.S. Provisional Patent Application No. 62/250,568 filed Nov. 4, 2015, which application is incorporated herein by reference in its entirety.

FIELD OF THE INVENTION

The present disclosure relates to a fabric or mesh construct, and a process for making same, that allows for early wound stability and then transitions to a more compliant state exhibiting a substantially constant macro-porous structure through the life of the implant to promote good tissue incorporation without bridging.

BACKGROUND

Absorbable and non-absorbable fibrous material are capable of providing a reinforcing scaffold for a range of membrane applications including tissue separation, hernia repair, peritoneum replacement, dura mater replacement, pelvic floor reconstruction, amongst others. Of these types of tissue repair and support, hernia repair is one of the most frequently performed surgical operations in the United States nearing approximately 1,000,000 procedures annually.

The vast majority of these repairs employ the use of synthetic surgical meshes that are comprised of various arrangements of absorbable and non-absorbable films, fibers, and yarns, and are primarily based on traditional knit and woven structures. Although these materials have reduced the frequency of hernia recurrence, rates remain high in the literature with up to 15% being reported for inguinal and incisional hernia repair. In addition, long-term complications such as chronic pain, increased abdominal wall stiffness, fibrosis, and mesh contraction persist following the use of current surgical meshes, which dramatically affects patient quality of life.

A movement in the development of synthetic hernia repair meshes is to create materials that contain a portion of absorbable materials. In practice, however, the absorbable components of these meshes do not serve to change the mechanics of hernia mesh within a physiologically-relevant range, but rather address a desire to reduce overall quantity of permanent material at the implant site. Additionally, the use of these partially absorbable meshes can result in new product failure modes because of the residual implant stiffness and reduced strength and stability associated with less permanent material.

Typically with partially absorbable meshes currently on the market, a significant loss in strength is seen upon degradation of the absorbable component as it is simply laid or plied into the knit pattern. Tear of the mesh, or tear strength, is becoming a critical feature as this is a typical failure mode for this type of surgical device. In addition, as hernia recurrence typically occurs at the margins of the mesh (i.e. where it is sutured into the native tissue), a significant loss in mesh suture pull-out strength may be a contributing factor to hernia recurrence at this location.

What is needed in the art is a mesh that leaves less residual material at the implant site in order to reduce chronic inflammatory responses. In addition, the art needs a mesh that is initially supportive, ultimately more compliant, and which does away with high tension transition between the flexible abdominal wall and the comparatively inflexible mesh/tissue complex.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

Briefly stated, the invention relates to meshes, and in particular to meshes that are useful in medical applications, such as surgical and hernia meshes. The meshes of the present disclosure are particularly well suited for use in medical applications.

In one embodiment, the present disclosure provides a partially absorbable mesh that comprises at least one bioabsorbable fiber and at least one biostable fiber. The mesh is partially absorbable in the sense that upon implantation of the mesh into a subject, the bioabsorbable fiber will degrade, or in other words, the bioabsorbable fiber will absorb into the host, leaving behind a mesh formed from the biostable fiber. The partially absorbable mesh has properties that are well suited to its initial implantation in the host, while the residual mesh formed from the biostable fiber has different properties that are well suited to a mesh that remains implanted in the host after a healing process has proceeded to a desired degree.

The bioabsorbable fiber and the biostable fiber are combined to form the partially absorbable mesh. When laid flat, the partially absorbable mesh is essentially a two-dimensional structure, having a substantial length, a substantial width, and a relatively small thickness. For convenience, the partially absorbable mesh may be described as having an X-direction and a perpendicular Y-direction, i.e., the X- and Y-directions are perpendicular to one another. In one embodiment, the mesh may be described as having a wale direction and a course direction, where the wale corresponds to the X-direction and the course corresponds to the Y-direction. In another embodiment, when the mesh is prepared on a knitting machine, the resulting mesh may be described as having a machine direction and a cross-machine direction, where the machine direction corresponds to the X-direction and the cross-machine direction corresponds to the Y-direction.

The partially absorbable mesh comprises pores. After the absorbable fiber(s) absorb or are otherwise removed or dissociated from the partially absorbable mesh, the residual mass of the partially absorbable mesh comprises biostable fiber. That biostable fiber is in the form of a biostable mesh. The biostable mesh likewise comprises pores. According to the present disclosure, a pore of a mesh can be characterized by a pore size, and a plurality of pores in a mesh can be characterized by an average pore size. Methods to determine pore size, and consequently average pore size, are described herein. Thus, the partially absorbable mesh comprises pores, and a plurality of the pores are characterized as having an average diameter.

Advantageously, one embodiment of the mesh is such that degradation of the partially bioabsorbable mesh does not significantly change the size of the pores that are present in the original mesh. For instance, the average diameter of a plurality of the pores changes by less than 25%, or less than 20%, or less than 15%, or less than 10%, or less than 5%, after removal of the bioabsorbable fiber from the partially absorbable mesh (in comparison to the original partially absorbable mesh). In other words, the biostable mesh that is a component of the partially absorbable mesh has an average pore size that is essentially the same as an average pore size of the partially absorbable mesh.

In part, this maintenance of pore size may be achieved according to the present disclosure by interweaving the bioabsorbable fiber around the pores that are formed by the biostable fiber rather than through those pores. In other words, the bioabsorbable fiber does not cross or otherwise occlude pores formed by the biostable fiber. Instead, the bioabsorbable fiber reinforces pores that are present in a biostable mesh. Therefore, when the bioabsorbable fiber undergoes bioabsorption in a host, the tissue adjacent to the mesh does not experience a change in its interaction(s) with the pores of the mesh. This is highly desirable since tissue tends to grow into the major pores of an adjacent mesh, and if these major pores maintain a constant or near-constant size, then the growing tissue is less like to be disturbed by bioabsorption of the partially absorbable mesh. Thus, in one embodiment, the bioabsorbable fiber is interwoven with the biostable fiber. In another embodiment, the bioabsorbable fiber reinforces a periphery of the pores of the partially absorbable mesh.

As noted above, in one embodiment, the biostable fiber forms a biostable mesh, and the biostable mesh is a component of the partially absorbable mesh. Optionally, the biostable fiber forms a biostable mesh having a weight of 35-70 g/m$^2$. Within this weight range, the biostable mesh has a desirably high strength to remain as a supporting mesh within the host, however it is not so large as to cause undesirable irritation within the host. This weight range is also desirable in that bioabsorbable fiber may be added to this weight of biostable mesh without creating a mesh that is heavyweight (>140 g/m$^2$).

The bioabsorbable fiber is preferably interwoven into the biostable mesh formed from the biostable fiber. This does not mean that the biostable mesh is necessarily formed first and the bioabsorbable fiber is added to the biostable mesh, although that is one option. However, it is also an option that the biostable mesh and the partially absorbable mesh are formed simultaneously, for example, by bringing the biostable and bioabsorbable fibers together at the same time as the partially absorbable mesh is formed. Thus, a statement that the bioabsorbable fiber is interwoven into the biostable mesh denotes a structure and not a method of making a mesh.

Likewise, the bioabsorbable fiber may be described as existing within the partially absorbable mesh in terms of a pattern. For instance, the bioabsorbable fiber may be present in a recognized stitch pattern, such as a pillar stitch. In one embodiment, the bioabsorbable fiber is present as a pillar stitch in the partially absorbable mesh. In another embodiment, a pillar stitch runs through the biostable mesh, where the pillar stitch is formed from bioabsorbable fiber, so that the resulting mesh is a partially absorbable mesh. In one embodiment, the bioabsorbable fiber in the form of a pillar stitch is interwoven with the biostable fiber.

In one embodiment, the partially absorbable mesh is anisotropic. In other words, the value of a mesh property as measured in the X-direction is different from the value observed for that same mesh property when it is measured in the Y-direction. As an example, the elongation of the mesh (a mesh property) may be greater in the Y direction than in the X direction, when that elongation is measured under standard conditions such as 16 N/cm. Optionally, the biostable mesh that forms a component of the partially absorbable mesh is, itself, anisotropic. However, in one embodiment, the addition of the bioabsorbable fiber induces or modifies anisotropic properties in the partially absorbable mesh that are not observed in the absence of the bioabsorbable fiber. As another example of anisotropy, in one embodiment the mesh of the present disclosure has an elongation in the X-direction when measured at 16 N/cm, where that elongation increases by at least 50%, or by at least 60%, or by at least 70%, or by at least 80%, or by at least 90%, after removal of the bioabsorbable fiber.

The structure of the mesh may also, or alternatively, be anisotropic. For example, in one embodiment the bioabsorbable fiber runs in the X-direction of the mesh. In another embodiment, the bioabsorbable fiber runs in the X-direction of the mesh and does not run in the Y-direction of the mesh. In yet another embodiment, the mesh comprises both colored and uncolored bioabsorbable fiber, where the colored bioabsorbable fiber runs in the X-direction of the mesh and does not run in the Y-direction of the mesh. Alternatively, in one embodiment the bioabsorbable fiber runs in the Y-direction of the mesh, while in another embodiment, the bioabsorbable fiber runs in the Y-direction of the mesh and does not run in the X-direction of the mesh. In yet another embodiment, the mesh comprises both colored and uncolored bioabsorbable fiber, where the colored bioabsorbable fiber runs in the Y-direction of the mesh and does not run in the X-direction of the mesh.

Having a colored thread run in one direction and not the perpendicular directions allows the surgeon to see an anisotropy in the mesh which may translate to anisotropic physical properties for the mesh. This allows the surgeon to position the mesh in a manner consistent with a preferred placement, without having to guess which direction provides which physical properties.

The biostable fiber component of the partially absorbable mesh does not degrade within the body after placement of the mesh in a patient's body. Examples of polymers that are biostable, and from which biostable fiber may be prepared, include polyolefins such as polypropylene and polyethylene. Optionally, the biostable fiber component may be replaced in whole or part with a slowly bioabsorbable fiber. A slowly bioabsorbable fiber maintains at least 90% of its physical properties for at least six months after placement in a host. Examples of slowly-absorbing bioabsorbable fibers include polylactic acid, PLLA, segmented block copolymer containing a majority of 1-lactide derived units, e.g., 88% 1-lactide and 12% trimethylene carbonate, and polyester such as poly(4-hydroxybuterate).

The bioabsorbable fiber component of the partially absorbable mesh does degrade within the body after placement of the mesh in a patient's body. That degradation may begin, for example, as soon as the mesh contacts the fluid environment of the patient, and typically is well underway within two weeks of placement. In one embodiment, the absorbable component of the mesh has completely degraded within the time period of 2-16 weeks. In another embodiment, the absorbable component of the mesh has completely degraded within the time period of 6-12 weeks. In one embodiment, the bioabsorbable fiber has completely dissolved after immersion of the partially absorbable mesh for 12 weeks in a phosphate buffer at 7.4 pH and 37° C.

The following are six additional exemplary embodiments of the present disclosure:

1. A mesh comprising: at least one bioabsorbable fiber; at least one biostable fiber; wherein the bioabsorbable fiber and the biostable fiber are co-knit to form a structure containing pores; and size of the pores remains substantially unchanged after absorption of the bioabsorbable fiber.
2. A process for forming a biostable/bioabsorbable composite comprising: using a stitch pattern to co-knit a biostable and a bioabsorbable fiber to form a structure with pores; and bioabsorption of the bioabsorbable fiber does not substantially change a size dimension of the pores within the structure.
3. A mesh comprising: at least one bioabsorbable fiber; at least one biostable fiber; wherein the bioabsorbable fiber and the biostable fiber are co-knit to form a pattern containing pores; and the bioabsorbable fiber reinforces the periphery of the pores.
4. A mesh comprising: at least one bioabsorbable fiber; at least one biostable fiber; wherein the bioabsorbable fiber and the biostable fiber are co-knit to form an initial pattern containing pores; and wherein the pattern remains substantially unchanged after absorption of the bioabsorbable fiber.
5. A mesh comprising: at least one bioabsorbable fiber; at least one biostable fiber; wherein the bioabsorbable fiber and the biostable fiber are co-knit to form a pattern containing pores; wherein the mesh remaining after degradation of the bioabsorbable fiber exhibits decreased Y direction elongation compared to the mesh before degradation of the bioabsorbable fiber; and wherein X direction elongation increases by approximately 100%, or in another embodiment, by greater than approximately 80%.
6. A mesh comprising: at least one bioabsorbable fiber; at least one biostable fiber; wherein the bioabsorbable fiber and the biostable fiber are co-knit to form a pattern containing pores; wherein the mesh remaining after degradation of the bioabsorbable fiber exhibits increased Y direction elongation compared to the mesh before degradation of the bioabsorbable fiber; and wherein X direction elongation increases by approximately 100%, or in another embodiment, by greater than approximately 80%.

In addition to providing meshes, the present disclosure also provides uses for meshes, and particularly medical uses for the meshes. For example, in one embodiment the present disclosure provides a method comprising placing a mesh according to the present disclosure in a patient, and particularly placing the mesh adjacent to tissue that would benefit from physical support. An example is a hernia, where a hernia occurs when an organ, intestine or fatty tissue squeezes through a hole or a weak spot in the surrounding muscle or connective tissue. The mesh of the present disclosure may be placed adjacent to or within the abdominal wall to reinforce a hole or weak spot in the muscle or connective tissue in order to provide a scaffold and support for healing to occur while protecting organs, intestines, or fatty tissue from passing through the abdominal wall. Examples of hernias which may be treated according to the methods of the present disclosure includes inguinal (occurs in the inner groin); femoral (occurs in the upper thigh/outer groin); incisional (occurs through an incision or scar in the abdomen), ventral (occurs in the general abdominal/ventral wall), umbilical (occurs at the belly button), and hiatal (occurs inside the abdomen, along the upper stomach/diaphragm). In one embodiment, the mesh is placed on the tissue in need of support, where the tissue is anisotropic in terms of its elongation, and the mesh is positioned so that the direction of mesh that exhibits the greater elongation matches the direction of tissue that exhibits the greater elonagation. In this way, the mesh better accommodates the movement of the tissue.

In addition to providing meshes and methods for their use, the present disclosure also provides methods for preparing a mesh. For example, in one embodiment biostable and bioabsorbable fiber are simultaneously used to form a mesh, where the biostable fiber forms a biostable mesh and the bioabsorbable fiber is interwoven with the biostable mesh at the same time that the biostable mesh is being formed. Optionally, the biostable fiber is introduced to the partially bioabsorbable mesh using a pillar stitch, i.e., the bioabsorbable fiber is interwoven in the form of a pillar stitch.

This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the drawings, and the claims.

BRIEF DESCRIPTION OF THE DRAWINGS

The construction designed to carry out the disclosure will hereinafter be described, together with other features thereof. The disclosure will be more readily understood from a reading of the following specification and by reference to the accompanying drawings forming a part thereof, wherein an example of the disclosure is shown and wherein:

FIG. 3B focuses on how to determine pore size of a mesh; and FIG. 3C focuses on an exemplary placement of bioabsorbable fiber within the mesh.

Figure 2:
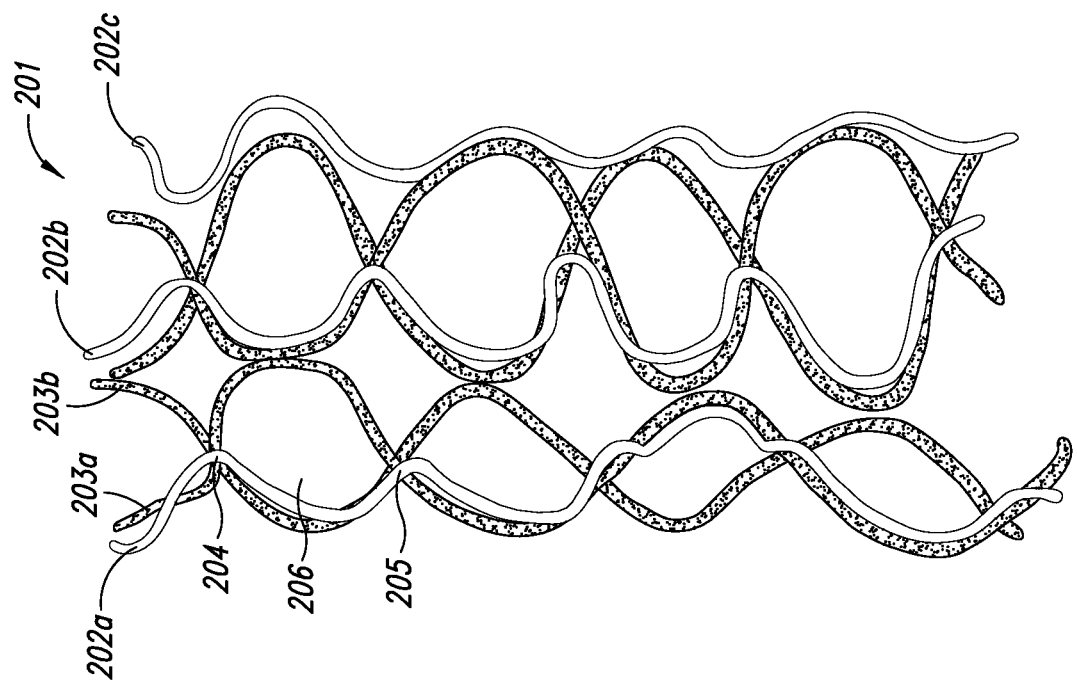
FIG. 2 shows a feature of a mesh construct pursuant to the current disclosure where one fiber type reinforces pores formed from a different fiber type.

It will be understood by those skilled in the art that one or more aspects of this disclosure can meet certain objectives, while one or more other aspects can meet certain other objectives. Each objective may not apply equally, in all its respects, to every aspect of this disclosure. As such, the preceding objects can be viewed in the alternative with respect to any one aspect of this disclosure. These and other objects and features of the disclosure will become more fully apparent when the following detailed description is read in conjunction with the accompanying figures and examples. However, it is to be understood that both the foregoing summary of the disclosure and the following detailed description are of a preferred embodiment and not restrictive of the disclosure or other alternate embodiments of the disclosure. In particular, while the disclosure is described herein with reference to a number of specific embodiments, it will be appreciated that the description is illustrative of the disclosure and is not constructed as limiting of the disclosure. Various modifications and applications may occur to those who are skilled in the art, without departing from the spirit and the scope of the disclosure, as described by the appended claims. Likewise, other objects, features, benefits and advantages of the present disclosure will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF THE INVENTION

With reference to the drawings, the disclosure will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

A benefit of partially absorbable meshes is that they may leave less residual material at the implant site, reducing chronic inflammatory responses associated with long-term implants. In one embodiment, the present disclosure provides a nonabsorbable mesh, i.e., a mesh formed from nonabsorbable fiber, which is also referred to herein as a biostable fiber and the corresponding mesh may be referred to herein as a biostable mesh, where the nonabsorbable mesh is combined with absorbable fiber. The absorbable fiber is interwoven into the mesh structure that is formed by the nonabsorbable fiber, to thereby provide a partially absorbable mesh.

The amount of residual material left at the implant site depends, in part, on the amount of nonabsorbable mesh that is present in the partially absorbable mesh of the present disclosure. Optionally, in this and the other embodiments disclosed herein, the nonabsorbable mesh component of the partially absorbable mesh of the present invention is an ultralight weight mesh, i.e., a mesh having a mass of less than 35 g/m$^2$ of mesh. As an alternative option, the nonabsorbable mesh component of the partially absorbable mesh of the present invention is a light weight mesh, i.e., a mesh having a mass in the range of 35-70 g/m$^2$ of mesh. In yet another option, the nonabsorbable mesh component of the partially absorbable mesh of the present invention is a standard weight mesh, i.e., a mesh having a mass of 70-140 g/m$^2$ of mesh. Another option provides that the nonabsorbable mesh component of the partially absorbable mesh of the present invention is a heavy weight mesh, i.e., a mesh having a mass of greater than 140 g/m$^2$ of mesh.

In one mesh embodiment, as discussed in greater detail herein, the average pore size of the partially absorbable mesh is essentially the same as the average pore size of the nonabsorable mesh which is a component of the partially absorbable mesh, when both meshes are under no external stress. In order to achieve this, the absorbable fiber may be interwoven around the periphery of the mesh pores that are formed from the nonabsorbable (biostable) fiber. Thus, the bioabsorbable fiber may be said to reinforce the periphery of the pores formed by the nonabsorbable fiber.

In one embodiment of the disclosure, a mesh is formed from at least one bioabsorbable fiber and at least one biostable fiber. In one embodiment, a mesh knit fabric may be produced that may be partially non-degradable, providing a permanent prophylactic protection against re-herniation. In one embodiment, a mesh of the present disclosure will stretch when it is being pulled, i.e., it exhibits elongation, however it is not elastic, i.e., it does not spring back to its original shape after it has been stretched.

The bioabsorable fiber may be a multifilament fiber or a monofilament fiber. In one embodiment the bioabsorbable fiber comprises, or consists of, multifilament fiber. In another embodiment, the bioabsorbable fiber comprises, or consists of, monofilament fiber. In yet another embodiment, both monofilament and multifilament bioabsorbable fiber is present in a partially absorbable mesh of the present disclosure.

The bioabsorbable fiber will lose its strength and/or its structural integrity after being implanted in a patient. The bioabsorbable fiber may also be referred to as a biodegradable fiber. An exemplary bioabsorbable fiber may be formed from a segmented polyaxial copolyester formed of an amorphous, polyaxial, polymeric initiator end-grafted with a mixture of ε-caprolactone and at least one cyclic monomer selected from the group consisting of l-lactide, dl-lactide, glycolide, and trimethylene carbonate, which forms crystallizable terminal segments. Meanwhile, the amorphous, polymeric initiator may be formed by the ring-opening polymerization of trimethylene carbonate in the presence of a catalyst, preferably stannous octanoate, and a monocentric polyfunctional initiator selected from the group consisting of triethanolamine, trimethylol-propane, and pentaerythritol. Alternatively, the amorphous, polymeric initiator may be formed by the ring-opening polymerization of a mixture of trimethylene carbonate and at least one monomer selected from p-dioxanone, ε-caprolactone, and 1,5-dioxepan-2-one.

As other options, the bioabsorbable fiber may be formed from silk protein, a linear, segmented lactide-derived copolyester, or a poly(3-hydroxyalkanoate). More specifically, the bioabsorbable fiber may be formed of a silk protein in the form of degummed, white Brazilian raw Bombyx mori silkworm fibers. Or the bioabsorbable fiber may be formed from a segmented copolymer formed from lactide and at least one monomer selected from glycolide, ε-caprolactone, trimethylene carbonate, p-dioxanone, or a morpholinedione; and/or (3) a poly(3-hydroxyalkanoate) selected from poly (3-hydroxybutyrate) and poly(3-hydroxybutyrate-co-3-hydroxyvalerate).

The biostable fibers may comprise at least one multifilament or monofilament yarn made from a polymer or polymers. In one embodiment the biostable fiber is a monofilament fiber. In another embodiment the biostable fiber is a multifilament. In yet another embodiment a mesh of the present disclosure is formed from both monofilament and multifilament biostable fiber.

Exemplary biostable fibers include polyethylene, such as ultrahigh molecular weight polyethylene (UHMWPE), polypropylene, polyamide such as an aliphatic polyamide (e.g., Nylon 6 and Nylon 66) and aromatic polyamide, polyether-ether ketone (PEK), and polyalkylene terephthalate such as polyethylene terephthalate (PET). Other biostable polymeric materials from which may be prepared a biostable fiber include poly(tetrafluoroethylene) which is also known as PTFE, and poly(hexafluoropropylene-VDF). The biostable fiber need not be made from an organic polymer, but may instead be formed from metal, e.g., stainless steel monofilament or twisted multifilament.

Possible weight ratios of biostable to bioabsorbable polymers may include 90:10, 80:20, 70:30; 60:40; and 50:50, as well as ranges selected from these values and options. In general, the bioabsorbable fiber restricts the elongation of the partially absorbable mesh, so that as the ratio of biostable:bioabsorbable fibers decreases from 90:10 to 50:50, the elongation of the partially absorbable mesh is decreased. This is advantageous because when the mesh is initially implanted into a host, at a time when the tissue is in dire need of support, it is desired that the mesh provide a high degree of support for the tissue that needs supporting. However, as that tissue heals, and is better able support itself and neighboring tissue, there is reduced need for the mesh to provide stable support. In fact it is advantageous for the mesh to have increased elongation in order to accommodate the elongation that the healed tissue naturally undergoes in the course of the host's normal activities. If the mesh continues to constrain the tissue, even after the tissue heals and is in less need of external support, then the healed tissue does not fully re-develop the ability to undergo natural elongation without undergoing damage.

The amount of initial support that is provided by the partially absorbed mesh of the present disclosure may be tailored, in part, by selecting an appropriate amount of the bioabsorbable fiber to be present in the partially absorbable mesh. In other words, as mentioned above, as the weight ratio of biostable to bioabsorbable polymers decreases from 90:10, to 80:20, to 70:30; to 60:40; and to 50:50, as well as ranges selected from these values and options, the mesh has relatively more bioabsorbable fiber, and accordingly provides relatively more support in terms of, e.g., less elongation. In one embodiment, the majority of the weight of the partially absorbable mesh is contributed by biostable fiber. In various optional embodiments, the bioabsorbable fiber contributes 10%, or 15%, or 20%, or 25%, or 30%, or 35%, or 40%, or 45%, or up to 49% of the weight of the partially absorbable mesh, where the rest of the weight is provided by the biostable fiber. The present disclosure provides for embodiments wherein the bioabsorbable fiber contributes an amount of weight to the partially absorbable mesh that falls within a range defined by a lower limit and an upper limit of weight percent, each of which may be selected from the afore-mentioned weight percent values. For example, the bioabsorbable fiber may contribute 10-49% of the weight of the partially absorbable mesh, or 10-40%, or 15-35% as two other options.

As used herein, fibers which are woven together are said to be interwoven. In other words, the fibers are combined in a manner such that one fiber winds or weaves around another fiber. The interwoven fibers may also be said to be interlaced or intertwined. Interwoven fibers may be created by hand sewing or machine knitting or sewing, or by an embroidery process, or any combination thereof. By being interwoven, and thus intimately a part of the partially absorbable mesh, the bioabsorbable fiber effectively impacts the physical properties of the partially absorbable mesh, such as the elongation of the mesh, as opposed to having the bioabsorbable fiber merely contacting the biostable mesh of the partially absorbable mesh.

In one embodiment the biostable and bioabsorbable fibers are combined by employing a knitting process wherein both of the biostable and bioabsorbable fibers are simultaneously fed into a knitting machine, i.e., in a one-step knitting process. Alternatively, the biostable fiber may be fed into a knitting machine to form a biostable mesh, and then the bioabsorbable fiber may be added to the biostable mesh by, e.g., a knitting process or a hand operated weaving process or an embroidery process.

Knitting is a technique for producing a fabric made from a fiber, yarn or thread. In weaving, threads typically run parallel either lengthwise (warp threads) or crosswise (weft threads). By contrast, knitted fabrics are formed from threads that follow a meandering path (a course), forming loops above and below the neutral path of the yarn. These meandering loops can be stretched in different directions providing potential for increased flexibility compared to woven mesh. For this reason, knitting was initially developed for materials that must be elastic or stretch in response to the user's motions. For comparison, woven materials stretch mainly along one or other of a related pair of directions that lie roughly diagonally between the warp and the weft, while contracting in the other direction of the pair (stretching and contracting with the bias), and are typically not very elastic, unless they are woven from stretchable material. In one embodiment, neither of the biostable nor the bioabsorbable fibers is notably elastic, i.e., the fibers have little or no elasticity.

There are two major varieties of knitting: weft knitting and warp knitting. In weft knitting, the wales are perpendicular to the course of the yarn and an entire fabric may be produced from a single yarn, by adding stitches to each wale in turn, moving across the fabric as in a raster scan. In contrast, in warp knitting, at least one yarn is required for every wale. For this reason, warp knit fabrics may provide more cut and tear resistance than weft knit fabrics.

In one embodiment, the partially absorbable mesh of the present disclosure is made by warp-knitting. Thus, in one embodiment, the partially absorbable mesh of the present disclosure comprises wales and courses. Suitable types of warp knitting patterns may include tricot, Milanese, raschel, marquisette, sand-fly, bobbie, crossed, herringbone, linen, cable, satin, atlas, Charmeuse, Voile, Akkordion, and English Net.

In one embodiment, the biostable fiber is formed into a stable knit construction using a 1 or 2-bar knit pattern. In a further embodiment, 2-bar knit patterns may be employed as they offer higher tear resistance. In another embodiment, the bioabsorbable fiber(s) may be added in a 1-bar knit pattern to stabilize/stiffen the structure, or through a 2-bar pattern.

In another embodiment, the bioabsorbable fiber(s) may be added to the biostable mesh using a pillar stitch, to provide a partially absorbable mesh of the present disclosure. In this embodiment, the bioabsorbable fiber does not form a mesh all by itself, i.e., if the biostable fiber were removed from the partially absorbable mesh of the present disclosure, the resulting structure would not be a mesh, but instead would be in the form of loosely associated bioabsorbable threads. Thus, for example, in one embodiment, the mesh of the present disclosure comprises a first fiber and a second fiber, the first and second fibers together arranged in a mesh structure; the first fiber arranged in a pillar stitch; and the second fiber forming a mesh and not arranged in a pillar stitch. The present disclosure also provides a process for forming a mesh comprising: incorporating a first fiber and a second fiber into a structure, the structure having a form of a mesh; wherein the first fiber is incorporated into the mesh using pillar stitching; and wherein the second fiber forms a biostable mesh and is not incorporated into the partially absorbable mesh using pillar stitching.

In a further embodiment, the pattern may be (Bar 1-Abs)/(Bar 2-Abs)/(Bar 3 Non-Abs)/(Bar 4 Non-Abs). In another embodiment, the pattern may be (Bar 1-Non-Abs)/(Bar 2-Abs)/(Bar 3-Non-Abs)/(Bar 4-Abs). Even further, the pattern may be (Bar 1-Non-Abs plied with Abs)/(Bar 2-Non-Abs). Many variations of the pattern are possible as known to those of skill in the art. In a preferred embodiment, the pattern may be (Bar 1-Non-Abs)/(Bar 2-Non-ABS)/(Bar 3-Abs).

Current synthetic technologies for mesh manufacture include creating: (1) co-knit constructs, e.g. fibers plied together in the same knit pattern or co-extruded to form a bi-component fiber; (2) co-knit textiles which rely on changes in the major pore to generate a compliance/mechanical transition; and (3) layered constructs which include a film to promote early stability. Optionally, the biostable and bioabsorbable fibers described herein may be formed into a textile product through a 1-step fabrication process as opposed to layering or other post-fabric forming processes that increase production complexity. For purposes of example only and not intended to be limiting, in one embodiment, a mesh or fabric may be knit in a 1-step process wherein the absorbable and non-absorbable yarns form a mesh in a co-knit pattern wherein the non-absorbable yarn forms the basis for the mesh as well as the major pore network of the mesh and the absorbable yarn does not occlude the major pore network by being knitted in a minimal knit pattern such as a pillar stitch. Thus, the one-step process is such that all knitting occurs in one step: all fibers/yarns feed into the construction during the knit fabrication process; they are not added in a later process step.

In one embodiment, the present disclosure provides a process for forming a mesh, the process comprising: using a stitch pattern to co-knit a biostable fiber and a bioabsorbable fiber to form a mesh structure with pores; where bioabsorption of the bioabsorbable fiber does not substantially change a size dimension of the pores within the structure.

In another embodiment, the present disclosure provides a process for forming a mesh comprising: using a stitch pattern to co-knit a biostable fiber and a bioabsorbable fiber to form a mesh structure with pores; wherein the bioabsorbable fiber is stitched with a pillar stitch.

In another embodiment, the present disclosure provides a process for constructing a mesh comprising: performing a one-step knitting process wherein biostable fibers and bioabsorbable fibers are simultaneously fed into a knitting machine to form the mesh; wherein the biostable fibers of the mesh are arrayed in a pattern comprising pores; and wherein the bioabsorbable fibers of the mesh are arrayed in a pattern that does not occlude the pores formed by the pattern of biostable fibers.

In one embodiment, the present disclosure provides a biostable mesh which is formed from biostable fiber. The bioabsorbable fiber may be woven into the biostable mesh such that the bioabsorbable fiber weaves around the biostable fiber that, independent of the bioabsorbable fiber, forms the biostable mesh.

Prior technologies in the area of surgical mesh do not allow for early wound stability that transitions to a more compliant state, in a manner that closely matches the extensional and anisotropic properties of the native abdominal wall, and which exhibits a macro-porous open pore structure throughout the life of the implant to promote good tissue incorporation without bridging, which may be defined as encapsulation of the mesh as a whole versus actual collagen integration into and through the pores of the mesh. Thus, there is "bridging" across the pores of the mesh.

For example, in one embodiment the present disclosure provides a mesh comprising: at least one bioabsorbable fiber and at least one biostable fiber; wherein the bioabsorbable fiber and the biostable fiber are combined to form a structure containing pores, the pores having an average size; and wherein the average size of the pores remains substantially unchanged after absorption of the bioabsorbable fiber.

As another example, the present disclosure provides a mesh comprising: at least one bioabsorbable fiber and at least one biostable fiber; wherein the bioabsorbable fiber and the biostable fiber are co-knit to form a pattern containing pores, the pores having a periphery; and the bioabsorbable fiber reinforces the periphery of the pores.

In another example, the present disclosure provides a mesh comprising: at least one bioabsorbable fiber and at least one biostable fiber; wherein the bioabsorbable fiber and the biostable fiber are co-knit to form an initial pattern containing pores; and wherein the initial pattern remains substantially unchanged after absorption of the bioabsorbable fiber.

In one more example, the present disclosure provides a mesh comprising: at least one biostable fiber in a form of a mesh structure containing pores, the pores having an average pore size when the mesh is at a resting state; at least one bioabsorbable fiber incorporated into the mesh; wherein the average pore size of the mesh does not change by more than 25%, or more than 20%, or more than 15%, or more than 10% upon removal of the bioabsorbable fiber from the mesh.

In one embodiment of the current disclosure, at least one absorbable fiber may be placed as a pillar stitch that confines a portion of a non-absorbable mesh. When the bioabsorbable component absorbs, the resulting, or final, mesh construction exhibits similar and often greater strength in many textile strength testing scenarios (ball burst, tensile, tear, suture pull-out). While not intended to be limiting and understanding ranges including the following are within the scope of this disclosure, in one embodiment, the following measurements were determined: Tensile (wale)=155.6 N (initial), 189.6 N (post-deg); Tensile (course)=188.3 N (initial), 202.8 N (post-deg); Tear (wale)=66.13 N (initial), 78.52 N (post-deg); Tear (course)=65.41 N (initial), 78.11 N (post-deg); Suture Pull-out (wale)=34.73 N (initial), 31.53 N (post-deg); Suture Pull-out (course)=33.79 N (initial), 32.52 N (post-deg); Ball Burst=362.35 N (initial), 341.85 N (post-deg). Typically with partially absorbable meshes currently on the market, a significant loss in strength is seen upon degradation of the bioabsorbable component as it is simply laid or plied into the knit pattern. Tearing of the mesh or tear strength is becoming a critical feature as this is a typical failure mode for this type of surgical device.

In one embodiment, fibers may be formed into a mesh structure with major pore size greater than 0.7 mm, major pore size greater than 1 mm, or major pore size greater than 2 mm. In one embodiment pore size of greater than 2 mm is preferred. Pore size is conveniently determined by placing a virtual circle inside the pore, where the largest circle which may fit within the pore is characterized by one or both of diameter and area. This diameter and area may be used as characterizing features of the corresponding pore, so that the pore itself may be described as having a distance (corresponding to the virtual circle diameter) and area (corresponding to the virtual circle area). The virtual circle should not be so large that it covers any of the fiber that defines the periphery of the pore. However, the circle should be sufficiently large that it comes right up next to the fiber(s) that defines the periphery of the pore, i.e., it is the largest circle that can fit wholly within the pore. The virtual circle is placed into the pore of a resting mesh, i.e., a mesh that is not being pulled or stretched in any direction, but instead is in an equilibrium state. Determination of pore size may occur using image analysis software.

The biostable mesh comprises a pattern of major pores, where the major pores are surrounded by, and thereby created by, the surrounding biostable fiber. The term "major pore" is used to distinguish from small gaps that may exist between regions of fiber, where these gaps may be referred to as "minor pores".

The circle, and accordingly the pore itself, may be described in terms of area, e.g., square millimeter ($mm^2$), or it may be described in terms of the diameter e.g., millimeter (mm), in either case being the largest circle that fits wholly within the pore. When described in terms of circle diameter, the pore size of a mesh of the present disclosure is, in various embodiments, greater than 0.1 mm, or greater than 0.5 mm, or greater than 0.6 mm, or greater than 0.7 mm, or greater than 0.8 mm, or greater than 0.9 mm, or greater than 1.0 mm, or greater than 1.1 mm, or greater than 1.2 mm, or greater than 1.3 mm, or greater than 1.4 mm, or greater than 1.5 mm, or greater than 1.6 mm, or greater than 1.7 mm, or greater than 1.8 mm, or greater than 1.9 mm, or greater than 2.0 mm, or greater than 2.1 mm, or greater than 2.2 mm, or greater than 2.3 mm, or greater than 2.4 mm, or greater than 2.5 mm, or greater than 2.6 mm, or greater than 2.7 mm, or greater than 2.8 mm, or greater than 2.9 mm, or greater than 3.0, or greater than 3.1 mm, or greater than 3.2 mm, or greater than 3.3 mm, or greater than 3.4 mm, or greater than 3.5 mm, or greater than 3.6 mm, or greater than 3.7 mm, or greater than 3.8 mm, or greater than 3.9 mm, or greater than 4.0 mm, up to about 5.0 mm, where the pore size may alternatively be described by a range of possible pore sizes defined by a lower limit and an upper limit of pore size, each limit selected from the afore-stated values, e.g. 0.7-2.0 mm, or 1.5-2.5 mm, as two options.

Pore size is dependent on knit pattern and post-knit processing. Varying pore sizes may be created by a range of warp knitting parameters including runner feed-in length (amount of yarn fed into the knit machine from the bars of yarn), knit patterns (i.e. stitch notation), and post-processing activities which include annealing. As listed above, different warp knit patterns may be used and varying the length of the stitch may also be used to result in different pore sizes. Finally, annealing is able to help impart different pore sizes as well as dimensional stability of the fabric. Different pore sizes can be created based on the level of extension or stretch applied to the fabric. However, as mentioned above, pore size is determined based on the properties of the resting mesh, i.e., a mesh that is not being pulled or stretched in any direction at the time of characterization but rather is sitting in an equilibrium state.

The meshes of the present disclosure includes pores, which may also be referred to as apertures. In one embodiment, the meshes include a plurality of pores of essentially the same size. In various embodiments, that plurality refers to at least 100, or at least 200, or at least 300, or at least 400, or at least 500 pores. The actual number of pores will depend on the total surface area of the mesh, and the average area size of the pores.

Optionally, the pores may be arranged in rows. In other words, the mesh may have a first row of pores, where a row of pores includes 10-100 or more pores, and the mesh also has a second row of pores which also includes 10-100 or more pores, where the first and second rows of pores are parallel to one another, i.e., the first and second rows do not cross one another. The meshes of the present disclosure may have multiple rows of pores, where the number of parallel rows of pores may optionally be at least 10, or at least 15, or at least 20, or at least 25, or at least 30, or at least 35, or at least 40, or at least 45, or at least 50, and where optionally the number of parallel rows may be described as falling within a range of possible values defined by an upper limit and a lower limit, where these limits may be selected from the afore-stated values, e.g., 10-50 rows. The number of rows of pores will depend, in part, on the area size of the mesh and the area size of the pores.

The meshes of the present disclosure may be anistropic. An anistropic mesh has different physical properties when that property is measured in the X-direction of the mesh, compared to when that property is measured in the perpendicular Y-direction of the mesh. For example, the mesh may exhibit greater elongation in the X-direction than in the Y-direction. More generally, in one embodiment, the present disclosure provides a mesh comprising: at least one bioabsorbable fiber and at least one biostable fiber; wherein the bioabsorbable fiber and the biostable fiber are combined to form mesh pattern comprising pores, the mesh having an X-direction and a perpendicular Y-direction; and wherein a tensile elongation in the X-direction of the mesh increases by about 100% after degradation of the bioabsorbable fiber. Optionally, the tensile elongation in the X-direction of the mesh increases by at least 80% after degradation of the bioabsorbable fiber. Optionally, the tensile elongation in the Y-direction of the mesh changes by less than 50% after degradation of the bioabsorbable fiber. Optionally, the tensile elongation in the Y-direction of the mesh changes by less than 25% after degradation of the bioabsorbable fiber. Optionally, the tensile elongation in the Y-direction of the mesh decreases after degradation of the bioabsorbable fiber.

Optionally, at least one of the X- and Y-direction changes elongation at 16 N/cm by at least 50% upon degradation of the bioabsorbable fiber.

In one embodiment of the disclosure, the absorption of the bioabsorbable fiber does not change or disrupt the pore size of the final configuration of the mesh. This may be accomplished by configuring the mesh so that the absorbable fiber or fibers restrict mobility of the mesh around the edges of the mesh but the absorbable fiber or fibers do not pass through the pore void space.

Figure 1:
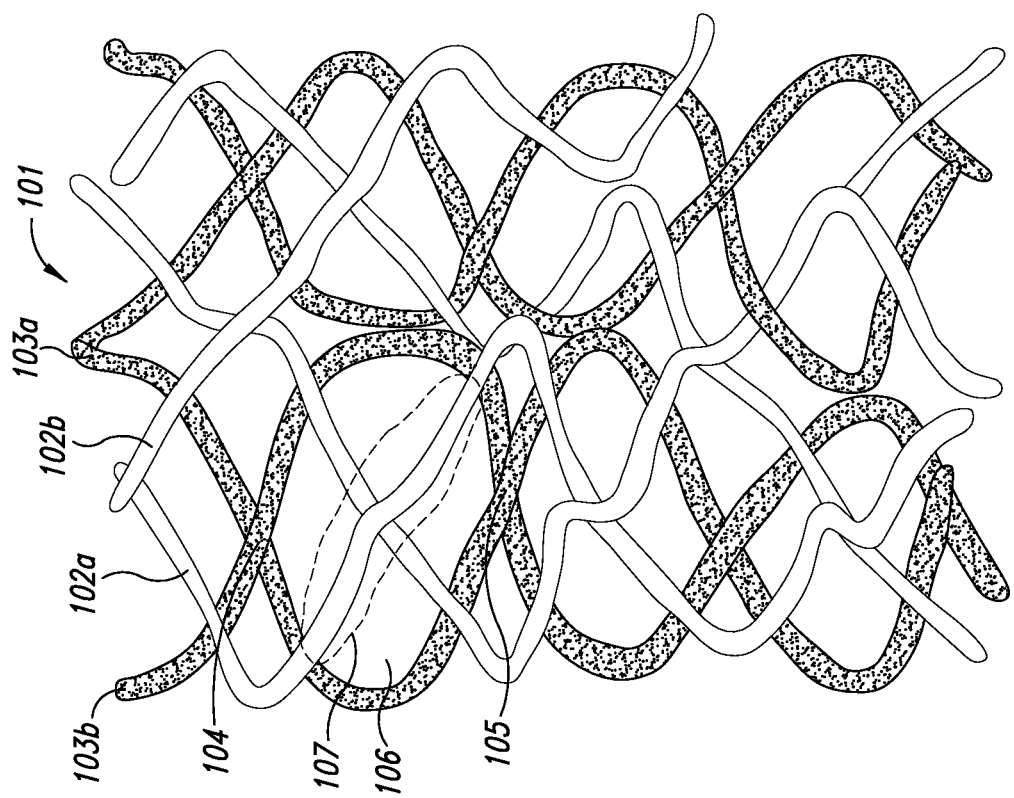
FIG. 1 shows a feature of a prior art mesh construct where one fiber type occludes pores formed from a different fiber type.

In one embodiment, a fabric made pursuant to the current disclosure may exhibit essentially the same pore size after the bioabsorbable component degrades. FIG. 1 shows a prior art mesh 101 formed from two different fiber types. One fiber type, 102a and 102b, is shown by white (non-shaded) fibers while the other fiber type, 103a and 103b, is shown by dark (speckled, shaded) fibers. Looking at the arrangement of fibers 103a and 103b, it is seen that they cross one another at multiple locations, e.g., at locations 104 and 105, so that between and including locations 104 and 105 the fibers 103a and 103b define a pore 106. This pore is partially occluded though, because a portion of the fiber 102a crosses the pore 106, where the crossing portion of fiber 102a is enclosed in a dashed line 107. Accordingly, an object which could have just barely fit through the pore 106 in the absence of the fiber 102a cannot, in the prior art mesh 101, fit through the pore 106 because fiber 102a is in the way. In FIG. 1, the portion 107 of thread 102a effectively divides pore 106 into two approximately equal sized apertures, so that the size of pore 106 is effectively cut in half by the presence of portion 107 bisecting pore 106. In prior art meshes, two different fiber types, e.g., 102a/102b and 103a/103b are commonly combined without actively controlling the impact one fiber type (in this case, 102a) has on the size of the pores formed by the other fiber type (in this case, 103a/103b). In this situation, and when one of the fiber types, e.g., fiber 102a, is a bioabsorbable fiber, then bioabsorption of the mesh leads to a change in the mesh's pore size since after it degrades, portion 107 is gone and no longer bisects pore 106.

FIG. 2, meanwhile, illustrates a possible mesh 201 of the current disclosure. FIG. 2 shows a mesh 201 formed from two different fiber types. One fiber type, 202a, 202b and 202c is shown by white (non-shaded) fibers while the other fiber type, 203a and 203b, is shown by dark (speckled, shaded) fibers. Looking at the arrangement of fibers 203a and 203b, it is seen that they cross one another at multiple locations, e.g., at locations 204 and 205, so that between and including locations 204 and 205 the fibers 203a and 203b define a pore 206. In contrast to the situation depicted in FIG. 1, this pore 206 is not partially occluded by any of fibers 202a, 202b or 202c because there is no portion of any of these fibers that crosses the pore 206. Instead, the fiber 202a essentially is interwoven around fibers 203a and 203b. Accordingly, an object which could have just barely fit through the pore 206 in the absence of the fiber 202a can, in the mesh 201 of the present disclosure, still readily fit through the pore 206 because fiber 202a is not in the way. In contrast to the situation shown in FIG. 1, no portion of thread 202a runs through pore 206 and accordingly the presence of thread 202a does not reduce the size of the pore 206 formed by threads 203a and 203b. In a mesh of the current disclosure, two different fiber types, e.g., 202a/202b and 203a/203b are commonly while actively controlling the impact one fiber type (in this case, 202a) has on the size of the pores formed by the other fiber type (in this case, 203a/203b). In this situation, and when one of the fiber types, e.g., fiber 202a, is a bioabsorbable fiber, then partial bioabsorption of the mesh leads to little or no change in the mesh's pore size since after it degrades, fiber 202a does not impact the size of pore 206. The absorbable yarn 202a is limited to the periphery of the major pore network formed by the non-absorbable yarn 203a/203b and does not cross or bisect the major pore network. Thus, when the bioabsorbable fibers are absorbed, the pore size remains substantially constant.

In one embodiment, it is desired that pore size not become smaller or obstructed upon partial degradation of the mesh. Benefits of pore size maintenance are that the device allows tissue ingrowth into a permanent scaffolding which promotes earlier remodeling and maturation of the newly deposited tissue at a compared to bioabsorbable scaffolding materials. Bioabsorbable scaffolding materials display temporal changes in pore size, mechanics, amongst other properties, requiring additional deposition of tissue at the wound site over a prolonged period. By maintaining the scaffolding structure (i.e. porosity and pore size) integration of the mesh into the surrounding tissue is able to occur at a faster rate due to the dependence and maintenance of the mesh structure.

Figure 3A:
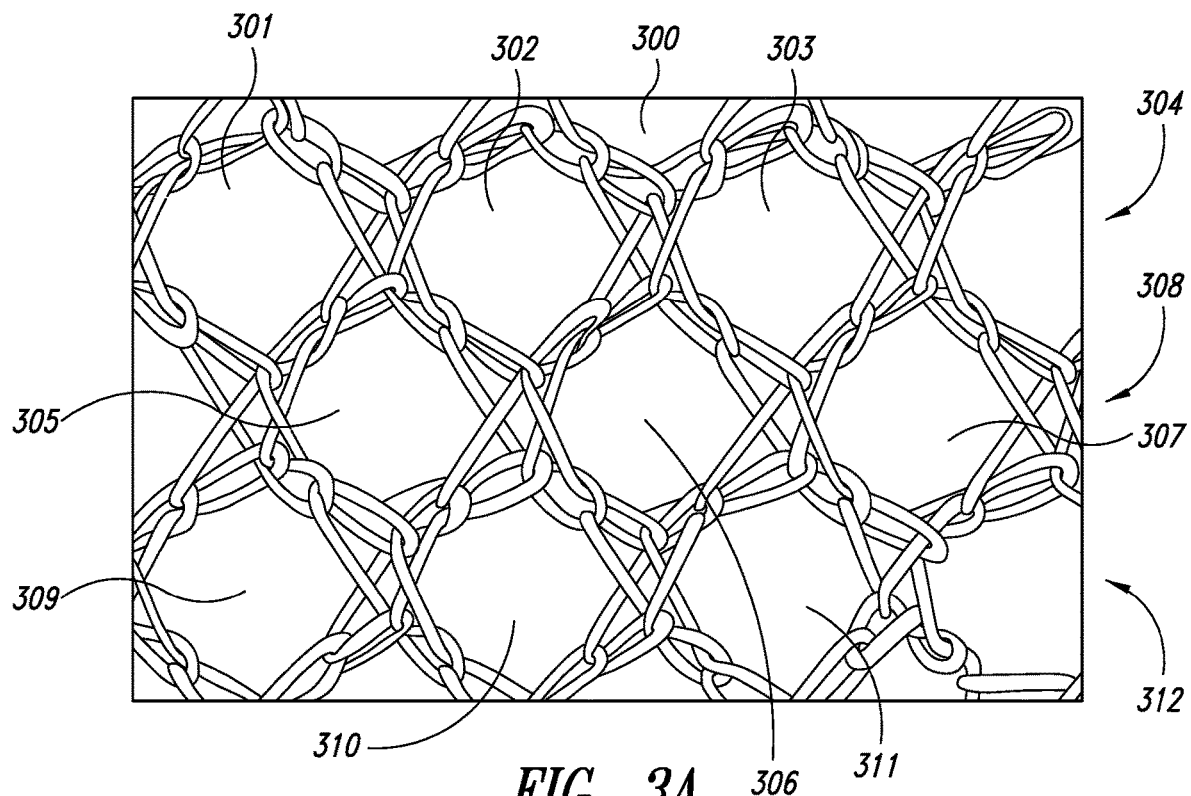
FIGS. 3A, 3B and 3C shows the same exemplary sample of a mesh of the present disclosure, where FIG. 3A focuses on the pores of the mesh.

FIG. 3A shows an exemplary portion of a mesh of the present disclosure. In FIG. 3A, the mesh 300 includes adjacent pores 301, 302 and 303 organized into a row 304. The mesh 300 also includes adjacent pores 305, 306 and 307 organized into a row 308. The mesh 300 also includes adjacent pores 309, 310 and 311 organized into a row 312. Noteworthy is that rows 304, 308 and 312 are parallel to one another, i.e., one row of pores does not cross another row of pores.

Figure 3B:
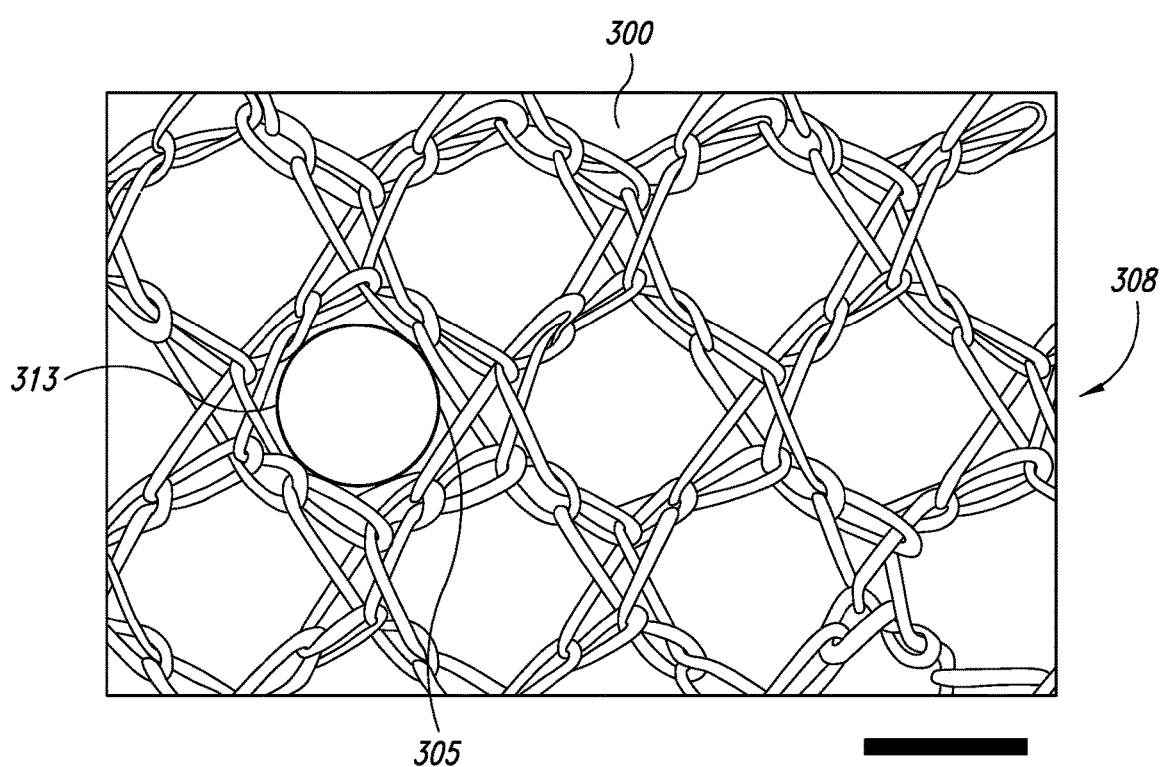

FIG. 3B shows how pore size may be determined. As shown in FIG. 3B, a circle 313 may be placed in a pore, e.g., pore 305, where the circle has the largest possible diameter which does not cause the perimeter of the circle to sit on top of the fibers that surround and define the pore. The diameter of this circle can be used to describe the size of the pore. In FIG. 3B the largest circle that fits into pore 305 has a diameter of 1900 µm. The pores of the mesh of FIG. 3B all have essentially the same size, so that the mesh of FIG. 3B may be said to have an average pore size of 1900 µm. This approach may be taken even though the pores themselves are not circular, but adopt a non-circular shape such as square, diamond, or hexagonal.

Figure 3C:
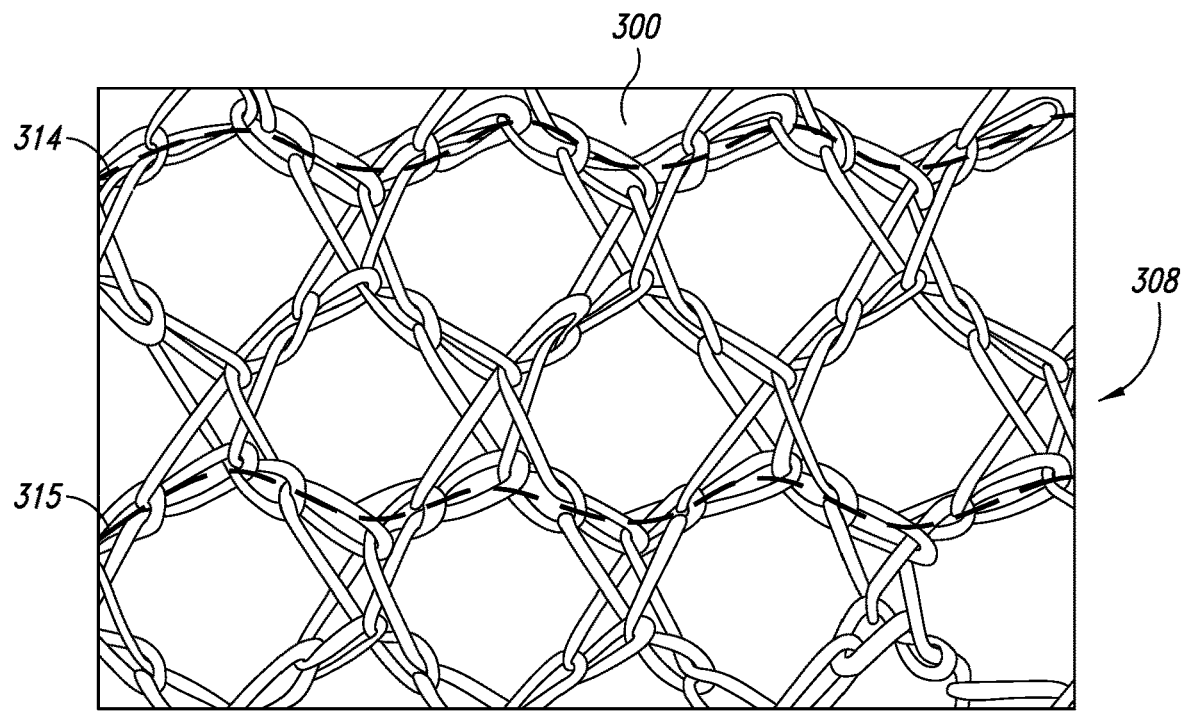

FIG. 3C shows how absorbable fiber 314 and 315 (dark dashed lines) may be combined with a mesh formed from biostable fiber (white thread). In FIG. 3C, the absorbable fiber 314 and 315 lies at the periphery of the pores, and does not cross or occlude any of the pores. As also shown in FIG. 3C, the bioabsorbable fibers 314 and 315 lie above and below, respectively, a pair of adjacent rows of pores, 304 and 308. In one embodiment, the present disclosure provides a mesh such as shown in FIG. 3C, where bioabsorbable fiber runs along the top and bottom of a pair of adjacent rows of pores. In another embodiment, the present disclosure provides a mesh where bioabsorbable fiber runs along the top or the bottom, but not both, of a row of pores. In another embodiment, bioabsorbable fiber runs between adjacent rows of pores.

Increased mesh/wound compliance may be accomplished by placing the absorbable component in a structurally supporting knit configuration. Therefore, upon degradation of this component the mesh shifts to a more compliant and less restrained knit construction. Resistance to tear propagation and suture pull-out may be controlled by the selected pattern that resists mesh unraveling. Reduced mesh contraction, the ability of cells to feel tension, is required to prevent a diseased state. For example, with a skin incision, tissue immediately surrounding the cut "loses" tension which tells the body something iswrong. Thus, placing a stiff construction over soft tissue keeps tissue from registering "load," and will preserve the sensation that something is wrong and tissue will contract in order to re-establish tension.

In one aspect of the current disclosure, absorbable material is placed to realize a significant increase in extension, following significant strength loss, in one direction of the mesh thus making the final construction anisotropic. Examination of tissue that comprises the abdominal wall indicates that this tissue is highly anisotropic: the tissue is oriented to stretch more in specific directions. The current disclosure mimics this function by allowing greater extension in the wale direction after the bioabsorbable component biodegrades.

In a further embodiment, the mesh or fabric made pursuant to this disclosure may be marked. For example, in one embodiment, a portion of the absorbable pillar stitches may be dyed a vibrant color, or otherwise made visible to the user, to indicate the direction of increased compliance following partial degradation of the selectively absorbable mesh device.

In a further embodiment the mesh as a whole, portions of the mesh, or selected fibers within the mesh, may be coated with a coating containing drugs to create a depot for localized delivery of active agents. For example, at least one bioactive agent may be selected from antimicrobial agents, anti-inflammatory agents, antineoplastic agents, anesthetic agents, tissue growth promoting agents or combinations of the above.

If a fabric is produced from the disclosure herein, it may be used as a surgical mesh, reconstruction mesh, hernia mesh, drug delivery fabric, support scaffold, reinforcing scaffold. For instance, the fabric may be: (1) a tissue engineering scaffold for repairing or replacing maxillofacial tissues; (2) a surgical mesh for repairing or tissue engineering of soft tissues; or (3) a hernial repair mesh comprising a knitted construct.

The current disclosure may also produce a fabric that may exhibit an initially relatively high modulus/low elasticity compared to native tissue, such as between 10-14% extension at physiological loading (16N/cm) initially in a ball burst testing configuration. After placement in vivo, the fabric may transition to a relatively extensible material compared to the initial fabric, and exhibit properties similar to native tissue. For purposes of example only and understanding ranges encompassing these amounts are considered within the scope of this disclosure, tensile (wale)=34.6% (initial) and 71.3% (post-deg) and/or tensile (course)=33.6% (initial), 39.5% (post-deg). When looking at native abdominal wall tissue, strength and elongation are very directional (i.e. stretches more in one direction than another). The mesh of the current disclosure accomplishes this characteristic. Therefore, a doctor may orient the mesh in the direction they want to become more extensible.

A fabric of the current disclosure may be relatively compliant and extensible after the bioabsorbable component degrades. Degradation may occur anywhere from 2-16 weeks depending on the bioabsorbable fiber(s) employed and the construction of the fabric. Degradation may be engineered such that it will not generate a modulus mismatch at the margins of the implant thereby reducing potential for re-herniation or complications at the implant site. Bioabsorption profiles may range from less than two weeks, two to six weeks, six to twelve weeks, from twelve to sixteen weeks, greater than twelve weeks, and greater than sixteen weeks. These profiles can be generated not only by the type of mesh designed but the yarn input as described above. For instance, a high glycolide absorbable component may exhibit strength loss between 2-4 weeks. In other embodiments, using a polydioxanone may yield a product where strength loss of the absorbable component occurs between 6-11 weeks. Quicker transition times may be more appropriate for a younger individual that heals faster. Longer transition time points may be necessary for older or overweight patients, that have poor healing ability.

This technology can be used for a range of markets that employ absorbable and/or nonabsorbable polymer systems. This can include but not limited to hernia repair mesh, implant support scaffold, tissue replacement devices, tissue augmentation devices, tissue scaffolding, drug delivery, among others.

A surgical mesh construction that is structurally rigid for the lifetime of the patient is not ideal and may be responsible for many of the long-term complications currently seen with mesh hernioplasty. The use of a unique selectively absorbable mesh design that modulates its properties in situ resulting in a highly compliant long-term construction and subsequent repair is preferred. In addition, poor tissue integration is linked to a number of clinical issues; therefore, a surface coating may be developed with a high degree of porosity and rapid degradation profile to increase the surface bioactivity of the developed mesh constructions.

Figure 4:
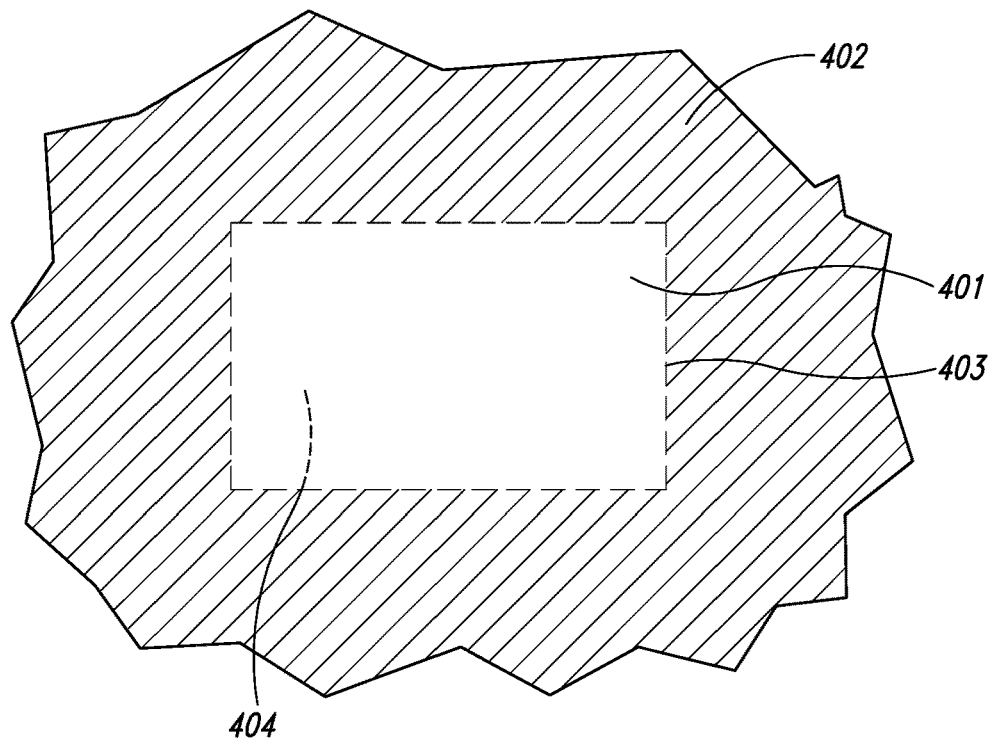
FIG. 4 shows a diagram depicting present day mesh hernioplasty.

FIG. 4 shows a diagram depicting a mesh hernioplasty situation, where a mesh 401 is fixed onto a tissue 402. The tissue 402 may be, e.g., abdominal wall tissue, and the mesh 401 may be fixed to the tissue using, e.g., suture or tacks. Mechanical testing of human abdominal wall samples reveals an elongation (sometimes referred to as elasticity) of approximately 18-32% at a physiological force of 16N/cm, and a maximum burst strength of 120 N. In contrast, a typical prior art surgical mesh has an elongation of less than 16% at a physiological force of 16N/cm, and a maximum burst strength of greater than 400 N. In this situation, due to differences in mechanical properties, e.g., the mesh 401 has a lower elasticity than the underlying tissue 402, the margins 403 of the mesh 401 encounter high shear and tensile forces. In contrast, the tissue 404 which is encompassed by the mesh 401, i.e., which is covered by the mesh 401, is stress shielded. The low stretching ability of a prior art mesh/tissue complex 401 is contrasted with a highly elastic abdominal wall tissue 402. This gives rise to high shear forces at the margins 403 of the mesh/tissue complex 401. The mechanical properties of prior art hernia meshes are vastly different than the mechanical properties of the native abdominal wall that is being repaired as depicted in FIG. 4.

Moreover, collagen deposition in and around these mesh constructs will inevitably further decrease the compliance of these constructions. In one study, mechanical testing of explanted polypropylene meshes indicated a 30x increase in rigidity when compared to the pristine device. This long-term lack of compliance will reduce patient mobility and increase discomfort at the implantation site as well as cause patient sensation of the mesh prosthesis. The meshes of the present disclosure address these problem as described herein, e.g., by providing a light weight nonabsorbable mesh with restrained stretching ability due to the placement of absorbable fiber in and around the nonabsorbable mesh.

An optional benefit of a mesh according to the present disclosure is that it transitions to a higher compliance state so that the ultimate mesh/tissue complex may be more compliant and will not result in a high tension transition between the flexible abdominal wall and a relatively inflexible mesh/tissue complex, resulting in high stresses and ultimately, in hernia applications, recurrence, foreign body sensations, and other associated complications. To generate materials that offer temporal properties and functions within a physiologically-relevant range, a combination of a stable, "permanent" fiber with an absorbable fiber can be knit into a mesh fabric wherein the absorbable fiber provides temporary mesh stability. The temporary mesh stability is observed, e.g., in that the component mesh formed from nonabsorbable fiber has a greater extensibility than does the original partially absorbable mesh. After implantation, the mesh transitions to a higher extensibility/higher compliance material as the absorbable fiber loses its mechanical integrity.

In the meshes of the present disclosure, the absorbable fiber restricts the extensibility of the mesh formed from the nonabsorbable fiber. The partially absorbable mesh thus has less extensibility than does the component nonabsorbable mesh, or in other words, the nonabsorbable mesh component is more extensible than the partially absorbable mesh.

The following are exemplary embodiments of the present disclosure:

1) A partially absorbable mesh comprising: at least one bioabsorbable fiber and at least one biostable fiber; wherein the bioabsorbable fiber and the biostable fiber are combined to form a partially absorbable mesh, the partially absorbable mesh having an X-direction and a perpendicular Y-direction; wherein the partially absorbable mesh comprises pores, and a plurality of the pores are characterized as having an average diameter; and wherein the average diameter of the pores changes by less than 25% after removal of the bioabsorbable fiber.
2) The mesh of embodiment 1 wherein the bioabsorbable fiber is interwoven with the biostable fiber.
3) The mesh of embodiments 1-2 wherein the bioabsorbable fiber reinforces a periphery of the pores.
4) The mesh of embodiments 1-3 wherein the biostable fiber forms a biostable mesh, and the biostable mesh is a component of the partially absorbable mesh.
5) The mesh of embodiments 1-4 wherein the biostable fiber forms a biostable mesh having a weight of 35-70 g/m2, and the biostable mesh is a component of the partially absorbable mesh.
6) The mesh of embodiments 1-5 wherein the bioabsorbable fiber is interwoven into a biostable mesh formed from the biostable fiber, where the bioabsorbable fiber is interwoven via a pillar stitch.
7) The mesh of embodiments 1-6 which is anisotropic.
8) The mesh of embodiments 1-7 wherein the bioabsorbable fiber induces an increased degree of anisotropy in the partially absorbable mesh compared to an anisotropy of the biostable mesh component of the partially absorbable mesh.
9) The mesh of embodiments 1-8 having a greater elongation in the Y-direction than in the X-direction when measured at 16 N/cm.
10) The mesh of embodiments 1-9 having an elongation in the X-direction when measured at 16 N/cm, the elongation increasing by at least 50% after removal of the bioabsorbable fiber.
11) The mesh of embodiments 1-10 wherein the bioabsorbable fiber runs in the X-direction of the mesh.
12) The mesh of embodiments 1-11 wherein the bioabsorbable fiber runs in the X-direction of the mesh and does not run in the Y-direction of the mesh.
13) The mesh of embodiments 1-12 comprising both colored and uncolored bioabsorbable fiber, where the colored bioabsorbable fiber runs in the X-direction of the mesh and does not run in the Y-direction of the mesh.
14) The mesh of embodiments 1-13 wherein the biostable fiber is prepared from a polymer selected from the group consisting of polyethylene, polyethylene terephthalate, and polypropylene.
15) The mesh of embodiments 1-14 wherein the bioabsorbable fiber has completely dissolved after immersion of the partially absorbable mesh after 12 weeks in a phosphate buffer at 7.4 pH and 37° C.
16) The mesh of embodiments 1-15 which is sterile.
17) The mesh of embodiments 1-16 which is packaged in a foil pouch.

The Example provided below further illustrates and exemplifies the present invention. It is to be understood that the scope of the present invention is not limited in any way by the scope of the following Example. In characterizing a mesh and/or components thereof, one or more of the following test protocols may be used: Area Weight by ASTM D3776M-09a Standard Test Methods for Mass Per Unit Area (Weight) of Fabric; Burst Load by ASTM D6797-07 Standard Test Method for Bursting Strength of Fabrics Constant-Rate-of-Extension (CRE) Ball Burst Test; Tensile and Elongation by ASTM D5034-09 Standard Test Method for Breaking Strength and Elongation of Textile Fabrics (Grab Test); Tear Resistance by ASTM D5587-14 Standard Test Method for Tearing Strength of Fabrics by Trapezoid Procedure.

EXAMPLE

A mesh was prepared from absorbable monofilament and non-absorbable monofilament. The absorbable monofilament was formed from an absorbable semi-crystalline tri-axial block copolyester which was prepared in a 2-step process as described in U.S. Pat. No. 7,129,319 using triethanolamine as the initiator and glycolide/trimethylene carbonate/l-lactide as the monomers in an 86/9/5 weight ratio. This polymer is commercially available from Poly-Med, Inc. in an oriented monofilament form as their product Glycoprene® 8609, having a diameter of 40-100 µm, a break strength of 90-120 KSI and a strength retention of about 10-20 days. Some additional properties of the monofilament are a fiber count of 1 (indicative of a monofilament rather than a multifilament); denier of 117 g/9000 m; breaking tenacity of 6.8 gf/denier (60.2 cN/tex; see ASTM D-3217-01a); ultimate elongation of 21%, and a color of translucent/off-white unless a dye has been added to the polymer prior to extrusion into a monofilament form, in which case the monofilament adopts the color of the dye. In the present Example, some monofilament colored with D&C Violet #2 was used to prepare the mesh.

The biostable monofilament was prepared from semi-crystalline polypropylene homopolymer. This polymer and/or monofilament forms thereof are commercially available from many suppliers, e.g., Mountainside Medical Equipment (Marcy, N.Y., USA); SMB Corp. (India); and Fitco (Oostende, Belgium). The polypropylene monofilament used in the present example was characterized by fiber count of 1 (indicating a monofilament rather than a multifilament); denier of 130 g/9000 m; a breaking tenacity of 6.1 gf/denier (54.0 cN/tex); an ultimate elongation of 21%; and a color of clear to translucent white.

A mesh was prepared by knitting together the absorbable and non-absorbable monofilaments. The knitting was performed in a one-step process using an 18-gauge Raschel Warp Knitting Machine, threaded 1 in-1 out. The knitting pattern was 2-bar sandfly pattern for polypropylene monofilament fibers and 1-bar pillar stitch of Glycoprene® 8609 monofilament fibers. Dyed (purple) fibers of Glycoprene® 8609 were used every 4th pillar stitch to provide a contrasting stripe. The product mesh was treated with heat to stabilize the mesh construction. The mesh was then sterilized by exposure to ethylene oxide, dried, and finally packaged in a hermetically sealed foil pouch.

The properties of the resulting mesh are shown in the Table, where initial properties refer to the properties of the mesh as retrieved from the hermetically-sealed foil pouch, and the terminal properties refer to the properties of the mesh after in vitro conditioning at 37° C. in 7.4 pH phosphate buffer for 12 weeks.

Figure 5A:
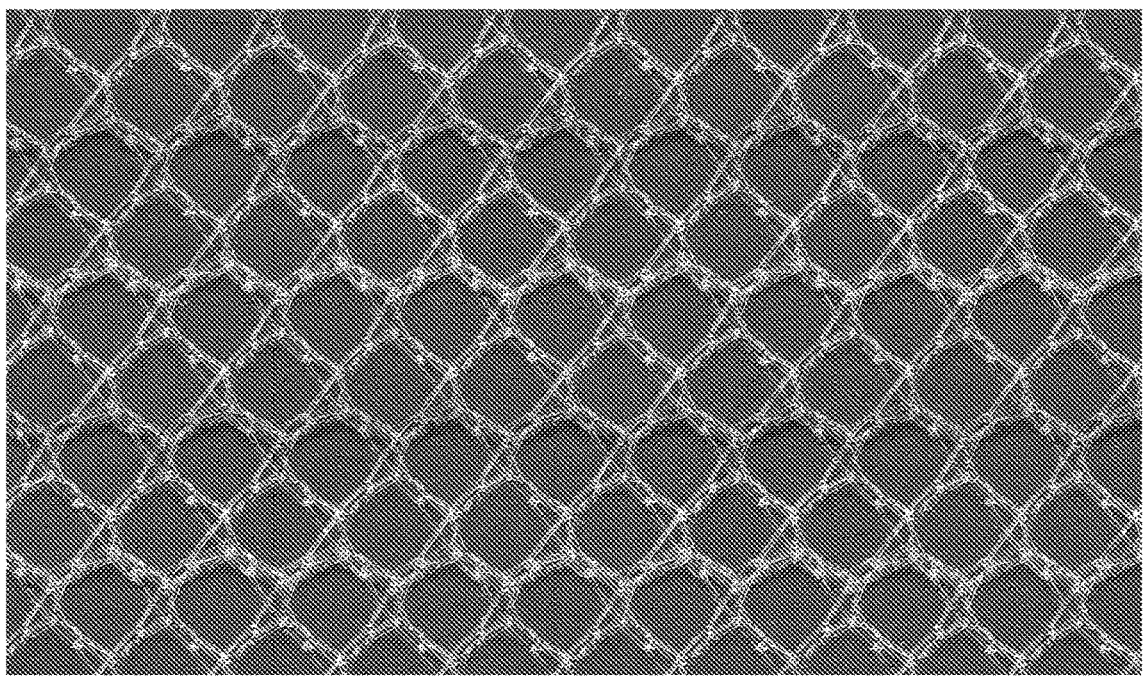
FIG. 5A is a photograph of a mesh of the current disclosure.
Figure 5B:
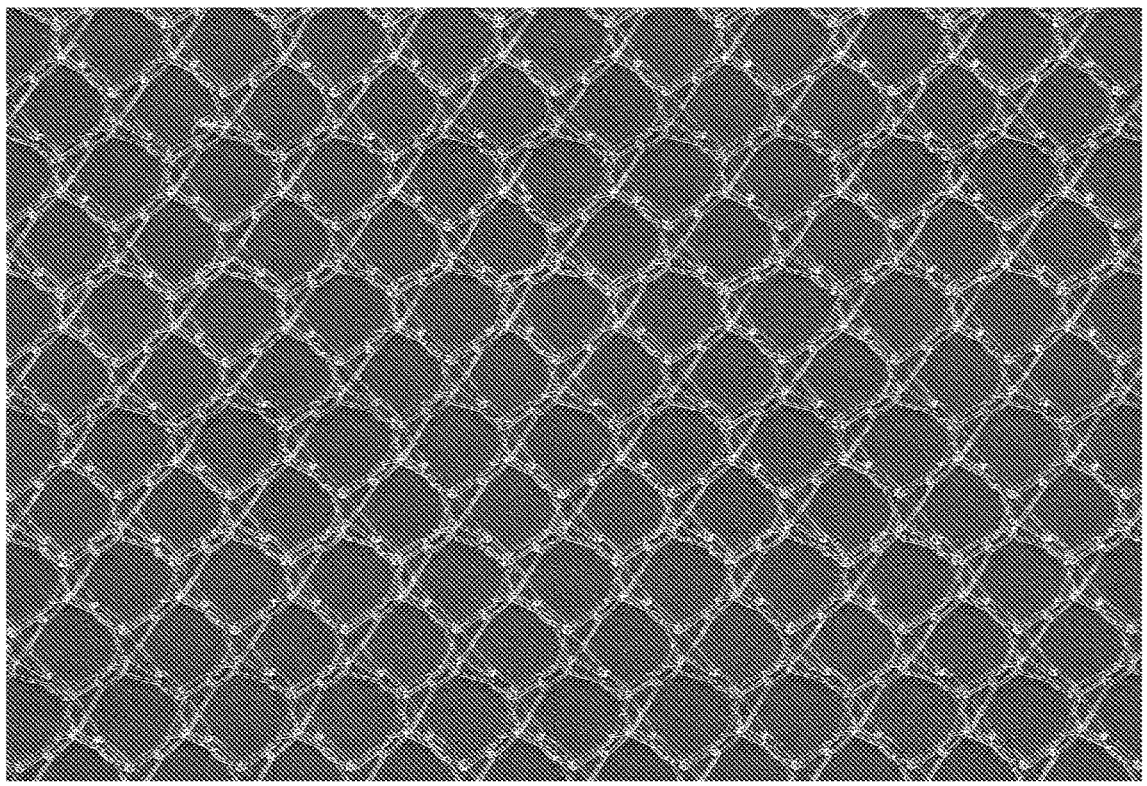
FIG. 5B is a photograph of a degraded mesh of the current disclosure which has lost the bioabsorbable component.

An image of the initial mesh is shown in FIG. 5A and an image of the terminal mesh is shown in FIG. 5B. Noteworthy is that the image of the initial mesh shows extra fiber running in an essentially horizontal direction, where that extra fiber is located both above and below every two adjacent rows of apertures. The extra fiber is not seen in the image of the terminal mesh because that extra fiber has dissolved away upon in vitro conditioning. Also noteworthy is that the size of the apertures is essentially unchanged between the initial and terminal conditions of the mesh.

| Table of Mesh Properties | | |
|---|---|---|
| Property | Initial | Terminal |
| Composition | 75% PP<br>25% Glycoprene ® 8609 | 100% PP |
| Area weight | 55 g/m$^2$ | 41 g/m$^2$ |
| Thickness | 0.6 mm | Not measured |
| Pore size | 2.05 mm | 1.94 mm |
| Ultimate tensile strength | 60N/cm, machine direction<br>67N/cm, cross machine direction | 72N/cm, machine direction<br>71N/cm, cross machine direction |
| Tensile Elongation at 16N/cm | 22%, machine direction<br>34%, cross machine direction | 43%, machine direction<br>38%, cross machine direction |
| Ultimate burst load | 319N | 306N |
| Burst Elongation at 16N/cm | 10% | 13% |
| Suture pullout load | 37N, machine direction<br>35N, cross machine direction | 35N, machine direction<br>35N, cross machine direction |
| Tear resistance, trapezoid | 65N, machine direction<br>34N, cross machine direction* | 66N, machine direction*<br>35N, cross machine direction* |

*Not considered "tearable" according to criteria of ASTM D5587-14

As seen from the data in the Table, the present disclosure provides a partially absorbable mesh (the "initial" mesh) wherein the bioabsorbable fiber induces an increased degree of anisotropy in the partially absorbable mesh compared to the biostable mesh component (the "terminal" mesh) of the partially absorbable mesh. The terminal mesh, which does not contain the bioabsorbable fiber, has tensile elongation at 16 N/cm which is approximately the same in each of the X-direction (machine direction) and the Y-direction (the cross machine direction): the average of the two elongation values is (43%+38%)/2=40.5%, and the deviation from this average is 43%−40.5%=2.5% where 2.5%/40.5%×100=6.2%. Thus, the elongation in either the X- or Y-direction is 6.2% from the average elongation of the terminal mesh. However, the initial mesh has an average elongation of (22%+34%)/2=28%, and the deviation from this average is 34%−28%=6.0% where 6.0%/28%×100=21.4%. Thus, although the terminal, biostable mesh has a slight degree of anisotropy in terms of elongation (6.2% variation between X- and Y-directions, compared to the average elongation), the initial, partially absorbable mesh has a much larger degree of anisotropy in terms of elongation (21.4% variation between X- and Y-directions, compared to the average elongation). Viewed another way, the terminal mesh has 5% more elongation in the X-direction than in the Y-direction (43%−38%), while the initial mesh has 12% more elongation in the Y-direction than in the X-direction (34%−22%). Thus, the present disclosure provides a partially absorbable mesh (e.g., the "initial" mesh) wherein the bioabsorbable fiber induces an increased degree of anisotropy in the partially absorbable mesh compared to the biostable mesh component (e.g., the "terminal" mesh) of the partially absorbable mesh. In one embodiment, the present disclosure provides a mesh having a greater elongation in the Y-direction than in the X-direction when measured at 16 N/cm, and in another embodiment, the present disclosure provides a partially absorbable mesh having an elongation in the X-direction when measured at 16 N/cm, where the elongation increases by at least 50% after removal of the bioabsorbable fiber (in the Example, the X-direction elongation increases by (43%−22%)/22%×100=95%, or approximately 100%.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Such documents may be incorporated by reference for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A partially absorbable mesh comprising:
a plurality of bioabsorbable fibers and a plurality of biostable fibers;
wherein the plurality of biostable fibers forms a biostable mesh, and the biostable mesh has an average pore size;
wherein the plurality of bioabsorbable fibers and the plurality of biostable fibers are combined to form the partially absorbable mesh, wherein the partially absorbable mesh comprises pores formed by the plurality of biostable fibers, and the plurality of bioabsorbable fibers is interwoven around and reinforces the pores, the partially absorbable mesh having an X-direction and a perpendicular Y-direction; and
wherein the partially absorbable mesh has an average pore size that is the same as the average pore size of the biostable mesh; and wherein the average diameter of the pores changes by less than 5% after removal of the plurality of bioabsorbable fibers; wherein the partially absorbable mesh is anisotropic.

2. The mesh of claim 1 wherein the plurality of biostable fibers forms the biostable mesh forms a biostable mesh having a weight of 35-70 g/m2.

3. The mesh of claim 1 wherein the plurality of bioabsorbable fibers is interwoven into the biostable mesh and the plurality of bioabsorbable fibers is interwoven via a pillar stitch.

4. The mesh of claim 1 wherein the plurality of bioabsorbable fibers induces an increased degree of anisotropy in the partially absorbable mesh compared to an anisotropy of the biostable mesh of the partially absorbable mesh.

5. The mesh of claim 1 having a greater elongation in the Y-direction than in the X-direction when measured at 16 N/cm.

6. The mesh of claim 1 having an elongation in the X-direction when measured at 16 N/cm, the elongation increasing by at least 50% after bioabsorption of at least a portion of the plurality of bioabsorbable fibers.

7. The mesh of claim 1 wherein the plurality of bioabsorbable fibers runs in the X-direction of the mesh.

8. The mesh of claim 1 wherein the plurality of bioabsorbable fibers runs in the X-direction of the mesh and does not run in the Y-direction of the mesh.

9. The mesh of claim 1, wherein the plurality of bioabsorbable fibers comprises both colored and uncolored bioabsorbable fibers, where the colored bioabsorbable fibers run in the X-direction of the mesh and do not run in the Y-direction of the mesh.

10. The mesh of claim 1 wherein the plurality of biostable fibers is prepared from a polymer selected from the group consisting of polyethylene, polyethylene terephthalate, and polypropylene.

11. The mesh of claim 1 wherein the plurality of bioabsorbable fibers has completely dissolved after immersion of the partially absorbable mesh after 12 weeks in a phosphate buffer at 7.4 pH and 37° C.

12. The mesh of claim 1 which is sterile.

13. The mesh of claim 1 which is packaged in a foil pouch.

* * * * *